US012622664B2

(12) United States Patent
Hsu et al.

(10) Patent No.: US 12,622,664 B2
(45) Date of Patent: May 12, 2026

(54) ACUTE RESPIRATORY DISTRESS SYNDROME EVALUATING METHOD AND SYSTEM THEREOF

(71) Applicant: China Medical University, Taichung City (TW)

(72) Inventors: Kai-Cheng Hsu, Hsinchu (TW); Wei-Cheng Chen, Taichung City (TW); Wei-Yang Yu, Taipei City (TW); Yu-Chao Lin, Taichung City (TW); How-Yang Tseng, Taichung City (TW); Chieh-Lung Chen, Taichung City (TW); Xin-Jie Liang, Taichung City (TW); Bo-Hao Yang, Taichung City (TW)

(73) Assignee: China Medical University, Taichung City (TW)

( * ) Notice: Subject to any disclaimer, the term of this patent is extended or adjusted under 35 U.S.C. 154(b) by 0 days.

(21) Appl. No.: 18/906,574

(22) Filed: Oct. 4, 2024

(65) Prior Publication Data

US 2025/0241607 A1 Jul. 31, 2025

(30) Foreign Application Priority Data

Jan. 31, 2024 (TW) ................................. 113103702

(51) Int. Cl.
*A61B 6/00* (2024.01)
*A61B 6/50* (2024.01)
(Continued)

(52) U.S. Cl.
CPC .............. *A61B 6/5217* (2013.01); *A61B 6/50* (2013.01); *G06T 7/0012* (2013.01); *G16H 50/20* (2018.01);
(Continued)

(58) Field of Classification Search
CPC ......... G06T 2207/20081; G06T 7/0012; G06T 2207/30061
See application file for complete search history.

(56) References Cited

U.S. PATENT DOCUMENTS

| | | |
|---|---|---|
| 5,873,824 A | 2/1999 | Doi et al. |
| 2021/0192727 A1* | 6/2021 | Ward .................... G06T 7/0012 |

(Continued)

FOREIGN PATENT DOCUMENTS

| | | | |
|---|---|---|---|
| CN | 115601289 A | 1/2023 | |
| KR | 20220169781 A * | 12/2022 | ........... G06V 10/469 |

OTHER PUBLICATIONS

Taoum et al., "Evidence-based model for real-time surveillance of ARDS," (Apr. 2019, Biomedical Signal Processing and Control vol. 50, Apr. 2019, pp. 83-91. (Year: 2019).*

(Continued)

*Primary Examiner* — Keith M Raymond
*Assistant Examiner* — Ashish S. Jasani

(57) ABSTRACT

An acute respiratory distress syndrome (ARDS) evaluating method includes an image preprocessing step, a lung infiltration determining step, a probability generating step and an evaluating step. The image preprocessing step includes inputting an X-ray image data to a first model to generate an X-ray partial image. The lung infiltration determining step includes inputting the X-ray partial image to a second model to generate a lung infiltration probability and a lung infiltration region image. The probability generating step includes inputting the lung infiltration probability, a blood inspection data, a vital signs data and a respiratory data to a third model to generate an ARDS suffering probability. The evaluating step includes calculating an evaluating result according to the lung infiltration region image and the ARDS suffering probability.

14 Claims, 4 Drawing Sheets

(51) Int. Cl.
  G06T 7/00    (2017.01)
  G16H 50/20   (2018.01)

(52) U.S. Cl.
  CPC ............... *G06T 2207/10116* (2013.01); *G06T 2207/20081* (2013.01); *G06T 2207/30061* (2013.01)

(56)       References Cited

U.S. PATENT DOCUMENTS

| | | | |
|---|---|---|---|
| 2023/0005603 A1* | 1/2023 | Rahman ............. | A61B 5/14542 |
| 2023/0029547 A1 | 2/2023 | Gehre et al. | |

OTHER PUBLICATIONS

Chiumello et al., "Lung Imaging and Artificial Intelligence in ARDS," (Jan. 5, 2024), J Clin Med. Jan. 5, 2024;13(2):305. (Year: 2024).*

* cited by examiner

S10

S12 — Image preprocessing step

S14 — Lung infiltration determining step

S16 — Probability generating step

S18 — Evaluating step

S10a

ACUTE RESPIRATORY DISTRESS SYNDROME EVALUATING METHOD AND SYSTEM THEREOF

RELATED APPLICATIONS

This application claims priority to Taiwan Application Serial Number 113103702, filed Jan. 31, 2024, which is herein incorporated by reference.

BACKGROUND

Technical Field

The present disclosure relates to an evaluating method and a system thereof. More particularly, the present disclosure relates to an acute respiratory distress syndrome (ARDS) evaluating method and a system thereof.

Description of Related Art

Acute respiratory distress syndrome (ARDS) is a severe disease with high mortality rate, the rapid clinical course progress thereof is the reason for the high mortality rate, and it's difficult to implement by early treatment. According to current research statistics, only 50% of the mild patients and 75% of the severe patients can be successfully diagnosed, and less than two-thirds of the patients can receive the treatment of the lung-protective ventilation.

Therefore, there is still a lack of an acute respiratory distress syndrome evaluating method and a system thereof that can be used to early diagnose, immediately treatment and dynamically adjust the acute respiratory distress syndrome according to the course thereof, so that it is indeed the expectation of people, and it's also the goal and direction of work for related industry.

SUMMARY

The present disclosure provides an acute respiratory distress syndrome (ARDS) evaluating method includes an image preprocessing step, a lung infiltration determining step, a probability generating step and an evaluating step. The image preprocessing step includes driving a processor to input an X-ray image data to a first model so as to generate an X-ray partial image. The lung infiltration determining step includes driving the processor to input the X-ray partial image to a second model so as to generate a lung infiltration probability and a lung infiltration region image. The probability generating step includes driving the processor to input the lung infiltration probability, a blood inspection data, a vital signs data and a respiratory data to a third model so as to generate an ARDS suffering probability. The evaluating step includes driving the processor to calculate the lung infiltration region image and the ARDS suffering probability so as to obtain an evaluating result.

The present disclosure provides an acute respiratory distress syndrome evaluating system includes a database and a processor. The database is use for accessing a first model, a second model, a third model, an X-ray image data, a blood inspection data, a vital signs data and a respiratory data. The processor is signally connected to the database and configured to perform an acute respiratory distress syndrome evaluating method, wherein the acute respiratory distress syndrome evaluating method includes an image preprocessing step, a lung infiltration determining step, a probability generating step and an evaluating step. The image preprocessing step includes inputting the X-ray image data to the first model so as to generate an X-ray partial image. The lung infiltration determining step includes inputting the X-ray partial image to the second model so as to generate a lung infiltration probability and a lung infiltration region image. The probability generating step includes inputting the lung infiltration probability, the blood inspection data, the vital signs data and the respiratory data to the third model so as to generate an ARDS suffering probability. The evaluating step includes calculating the lung infiltration region image and the ARDS suffering probability so as to obtain an evaluating result.

BRIEF DESCRIPTION OF THE DRAWINGS

The present disclosure can be more fully understood by reading the following detailed description of the embodiment, with reference made to the accompanying drawings as follows.

DETAILED DESCRIPTION

The embodiment will be described with the drawings. For clarity, some practical details will be described below. However, it should be noted that the present disclosure should not be limited by the practical details, that is, in some embodiment, the practical details is unnecessary. In addition, for simplifying the drawings, some conventional structures and elements will be simply illustrated, and repeated elements may be represented by the same labels.

It will be understood that when an element (or device) is referred to as be "connected to" another element, it can be directly connected to other element, or it can be indirectly connected to the other element, that is, intervening elements may be present. In contrast, when an element is referred to as be "directly connected to" another element, there are no intervening elements present. In addition, the terms first, second, third, etc. are used herein to describe various elements or components, these elements or components should not be limited by these terms. Consequently, a first element or component discussed below could be termed a second element or component.

Figure 1:
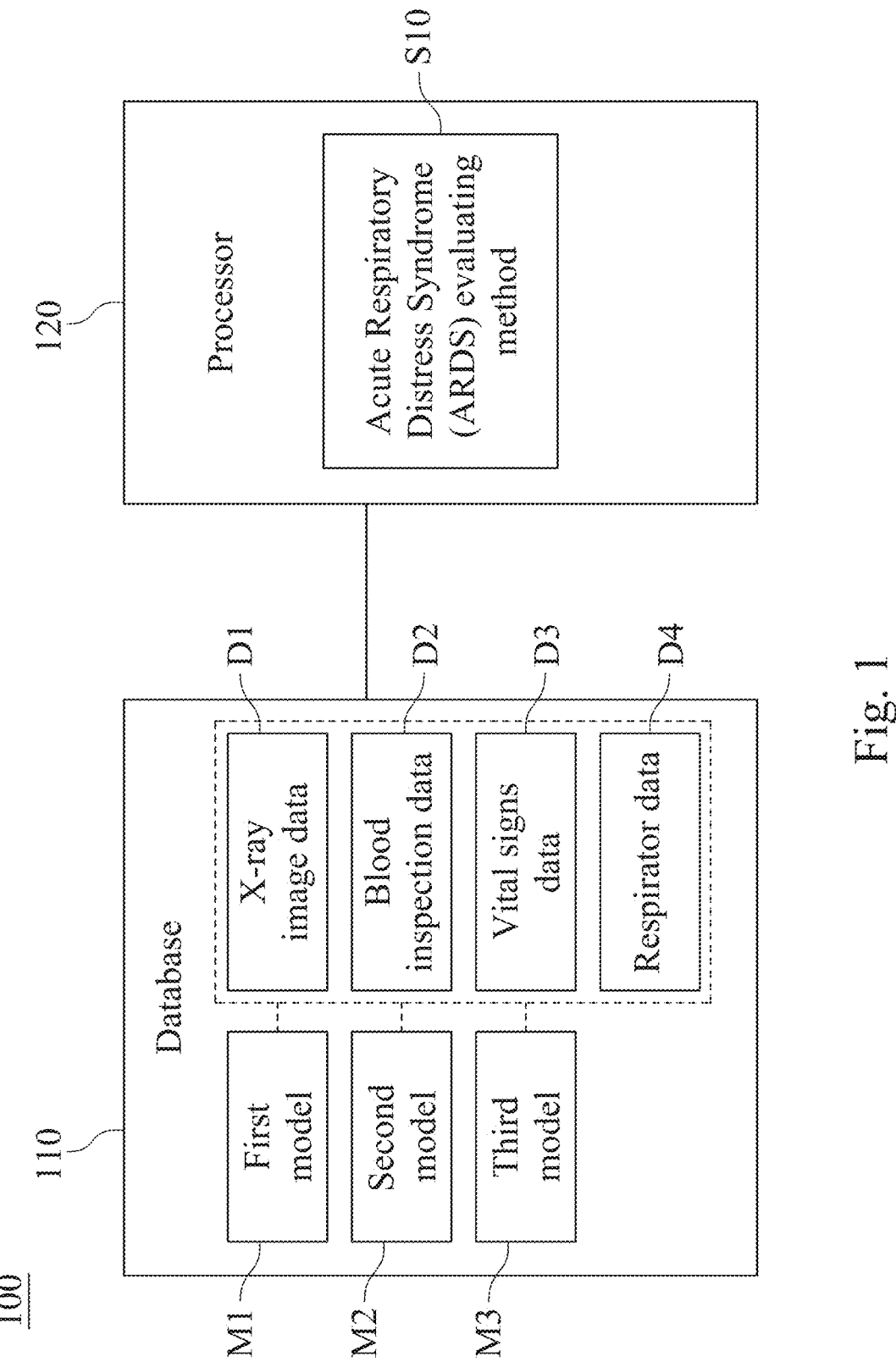
FIG. 1 is a block diagram of an acute respiratory distress syndrome evaluating system according to the first example of the present disclosure.

Reference is made to FIG. 1, which is a block diagram of an acute respiratory distress syndrome evaluating system 100 according to the first example of the present disclosure. The acute respiratory distress syndrome evaluating system 100 includes a database 110 and a processor 120. The database 110 is used for accessing a first model M1, a second model M2, a third model M3, an X-ray image data D1, a blood inspection data D2, a vital signs data D3 and a respiratory data D4. The processor 120 is signally connected to the database 110 and configured to perform an acute respiratory distress syndrome evaluating method S10.

In particular, the database 110 includes a random access memory (RAM) or other types of dynamic storage devices that can store the information and the instructions which can be accessed by the processor 120. The processor 120 can include any types of processors or microprocessors, but the present disclosure is not limited thereto. For example, the X-ray image data D1 can be an A-P view image or a P-A view image captured by the chest X-ray inspection. The blood inspection data D2 can include the data of partial pressure of oxygen (pO$_2$), fraction of inspired oxygen (FiO$_2$), oxygenation ratio (PaO$_2$/FiO$_2$ Ratio; P/F Ratio), platelet, hemoglobin (Hb), troponin, monocytes and eosino-phils. The vital signs data D3 can include the data of breath, diastolic blood pressure (DBP), systolic blood pressure (SBP) and body temperature. The respiratory data D4 can include the data of saturation of peripheral oxygen (SPO$_2$), respiration rate (Rate), mean airway pressure (Pmean) and positive end expiratory pressure (PEEP), but the present disclosure is not limited thereto. The steps of the acute respiratory distress syndrome evaluating method S10 will be described in more detail examples below.

Figure 2:
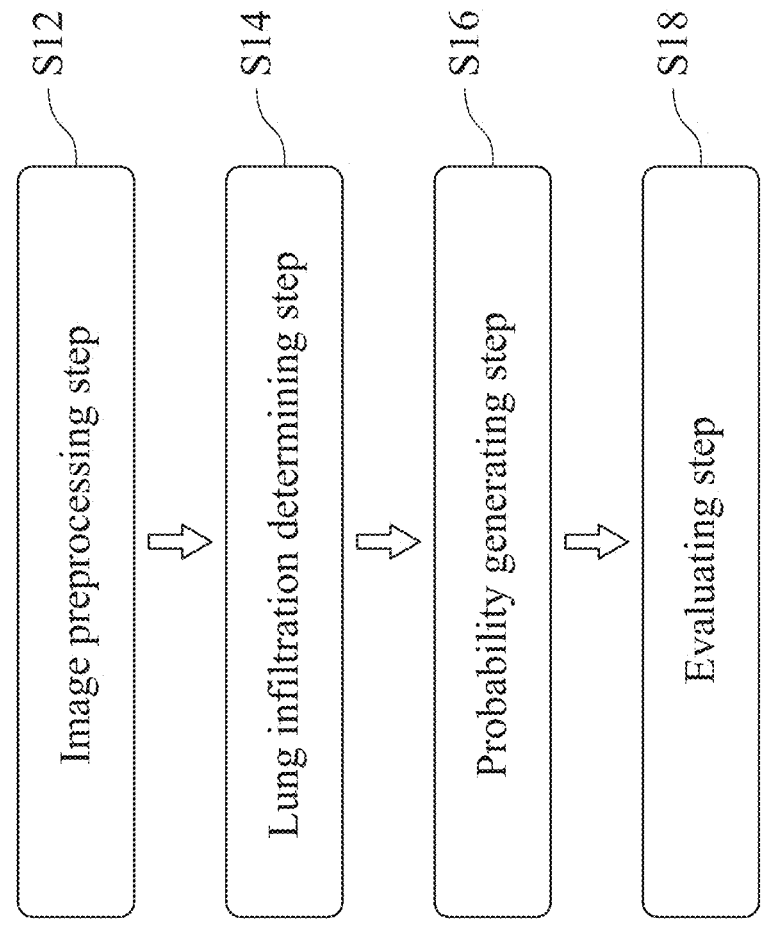
FIG. 2 is a flow chart of an acute respiratory distress syndrome evaluating method according to the second example of the present disclosure.
Figure 3:
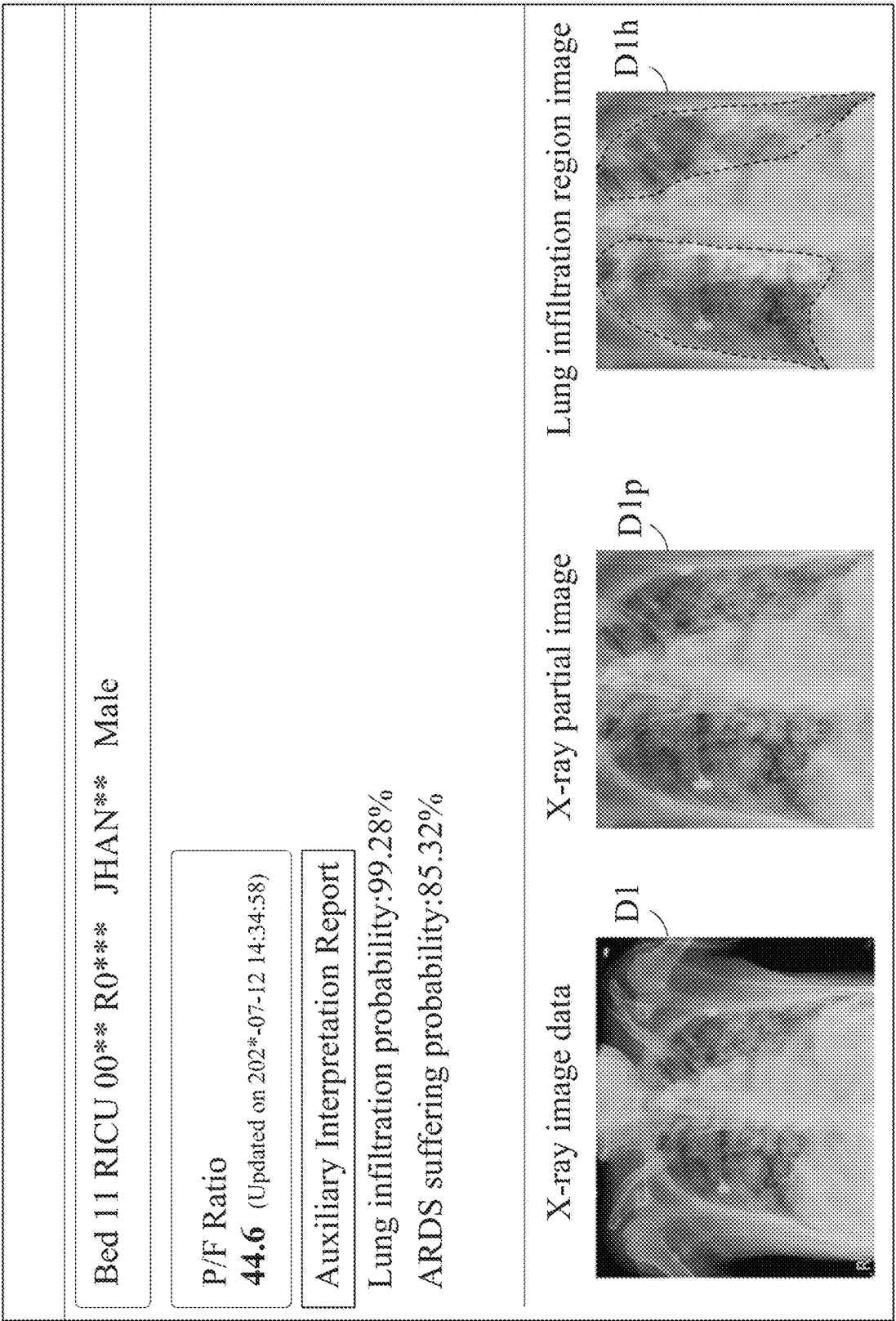
FIG. 3 is a schematic view of an evaluating result of the acute respiratory distress syndrome evaluating method of FIG. 2.

Reference is made to FIG. 1 to FIG. 3, wherein FIG. 2 is a flow chart of an acute respiratory distress syndrome evaluating method S10 according to the second example of the present disclosure, FIG. 3 is a schematic view of an evaluating result D5 of the acute respiratory distress syndrome evaluating method S10 of FIG. 2. The acute respi-ratory distress syndrome evaluating method S10 includes an image preprocessing step S12, a lung infiltration determin-ing step S14, a probability generating step S16 and an evaluating step S18. The image preprocessing step S12 includes inputting the X-ray image data D1 to the first model M1 so as to generate an X-ray partial image D1p. The lung infiltration determining step S14 includes inputting the X-ray partial image Dip to the second model M2 so as to generate a lung infiltration probability and a lung infiltration region image D1h. The probability generating step S16 includes inputting the lung infiltration probability, the blood inspection data D2, the vital signs data D3 and the respira-tory data D4 to the third model M3 so as to generate an ARDS suffering probability. The evaluating step S18 includes calculating the lung infiltration region image D1h and the ARDS suffering probability so as to obtain the evaluating result D5.

In the image preprocessing step S12, the first model M1 can be an image-cutting deep learning model, and the X-ray image data D1 is cut by the image-cutting deep learning model. In detail, the X-ray image data D1 can be cut so as to obtain an X-ray image including only the lung region, and a size of the X-ray image including only the lung region can be adjusted to be uniform size so as to obtain the X-ray partial image D1p. In other words, the X-ray partial image D1p can consist of a lung region image. Further, in the second example, the first model M1 can be an Efficient-UNet model, but the present disclosure is not limited thereto.

In the lung infiltration determining step S14, the lung infiltration probability can be obtained by identifying the lung region of the X-ray partial image D1p by the second model M2, and the lung infiltration region image D1h with labels of the infiltration region can be obtained simultane-ously. As shown in FIG. 3, the infiltration region of the lung region is outlined with dashed lines in the lung infiltration region image D1h. In other examples of the present disclo-sure, the infiltration region and the degree of infiltration in the lung of the lung infiltration region image D1h can also be presented by a heat map with different colors, but the present disclosure is not limited thereto.

In the probability generating step S16, the ARDS suffer-ing probability can be assessed by the third model M3 based on the lung infiltration probability, the blood inspection data D2, the vital signs data D3 and the respiratory data D4. In the second example, the third model M3 can be an extreme Gradient Boosting model, but the present disclosure is not limited thereto.

As shown in FIG. 3, the identity information (for example, bed, sex), the oxygenation ratio (R/F Ratio) of the blood inspection data D2, the lung infiltration probability, the ARDS suffering probability, the X-ray image data D1, the X-ray partial image Dip and the lung infiltration region image D1h of the patient are shown. In the evaluating step S18, the lung infiltration region image D1h and the ARDS suffering probability can be assessed whether the patient suffers the acute respiratory distress syndrome or not. There-fore, the acute respiratory distress syndrome evaluating method S10 of the present disclosure can immediately diagnose the ARDS suffering probability according to the disease course, so that the corresponding treatment can be timely provided.

Figure 4:
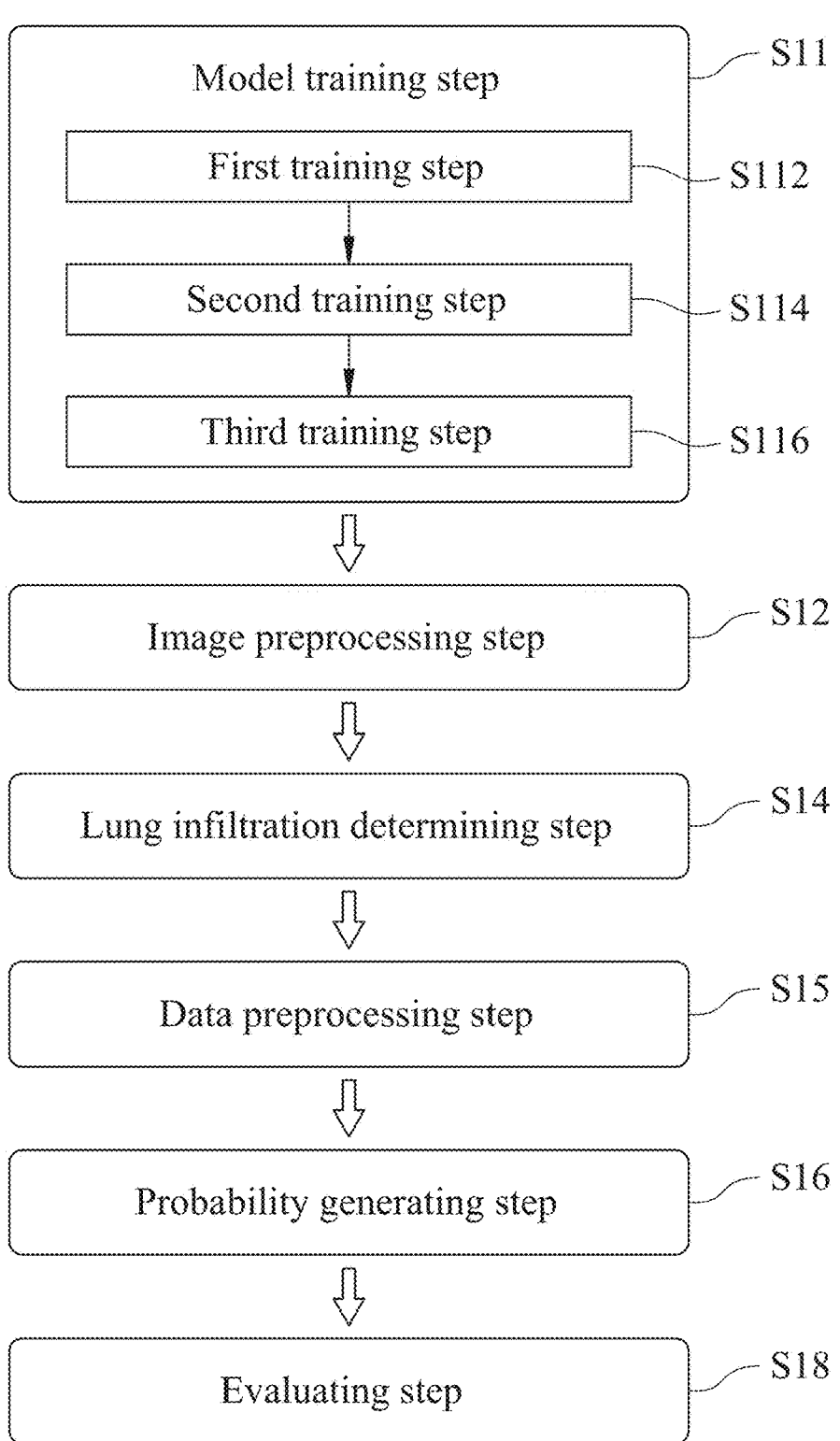
FIG. 4 is a flow chart of an acute respiratory distress syndrome evaluating method according to the third example of the present disclosure.

Reference is made to FIG. 1 to FIG. 4, wherein FIG. 4 is a flow chart of an acute respiratory distress syndrome evaluating method S10a according to the third example of the present disclosure. The acute respiratory distress syn-drome evaluating method S10a includes a model training step S11, an image preprocessing step S12, a lung infiltration determining step S14, a data preprocessing step S15, a probability generating step S16 and an evaluating step S18. In the third example, the image preprocessing step S12, the lung infiltration determining step S14, the probability gen-erating step S16 and the evaluating step S18 of the acute respiratory distress syndrome evaluating method S10a can be respectively the same to the image preprocessing step S12, the lung infiltration determining step S14, the prob-ability generating step S16 and the evaluating step S18 in the second example, and it will not be described again herein. In particular, the acute respiratory distress syndrome evaluat-ing method S10a can further include the model training step S11 and the data preprocessing step S15.

The model training step S11 includes a first training step S112, a second training step S114 and a third training step S116. The first training step S112 includes training the first model M1 based on an X-ray image training set and a lung X-ray image training set. The second training step S114 includes training the second model M2 based on a lung infiltration X-ray image training set and the lung X-ray image training set. The third training step S116 includes training the third model M3 based on a plurality of medical datasets, wherein each of the plurality of medical datasets includes the lung infiltration probability, the blood inspec-tion data D2, the vital signs data D3 and the respiratory data D4.

In other words, the model training step S11 includes the establishing processes of the first model M1, the second model M2 and the third model M3. In the first training step S112, the first model M1 is trained based on a plurality of unprocessed chest X-ray images (that is, the X-ray image training set) and a plurality of labelled chest X-ray images (that is, the lung X-ray image training set, and the labelled chest X-ray images are with the labels of the lung region), the first model M1 can be used to cut and obtain the X-ray partial image D1p of the lung region.

In the second training step S114, the second model M2 is trained based on the labelled chest X-ray images in the lung X-ray image training set and a plurality of chest X-ray images labelled as the lung infiltration (that is, the lung infiltration X-ray image training set). In other examples of the present disclosure, the lung X-ray image training set and the lung infiltration X-ray image training set also can be input to the first model M1 in the second training step S114 first, and the aforementioned images can be further trained after the lung region thereof is obtained by the cutting by the first model M1 so as to train the second model M2.

Further, the second model M2 can be an Efficient-Net model and can include a Convolutional Block Attention Module (CBAM). By adding the Convolutional Block Attention Module to the Efficient-Net model, the perform of the second model M2 can be focused on the region of the lung infiltration, and thus the lung infiltration region image D1$h$ generated by the second model M2 can be more accurately to label the region of the lung infiltration.

The third training step S116 can further include calculating the plurality of medical datasets so as to obtain an average value (Means), a standard deviation (standard deviation; std), a skewness value (Skewness) and a kurtosis value (Kurtosis) of at least one of the blood inspection data D2, the vital signs data D3 and the respiratory data D4 of each of the plurality of medical datasets, and then the third model M3 is trained based on the plurality of medical datasets and the average value, the standard deviation, the skewness value and the kurtosis value of the at least one of the blood inspection data D2, the vital signs data D3 and the respiratory data D4 of each of the plurality of medical datasets. For example, the vital signs data D3 and the respiratory data D4 include a plurality of immediate feature parameters, and a plurality of values of the same feature parameter may be collected within a specific time. The third training step S116 of the present disclosure can calculate the aforementioned of the average value, the standard deviation, the skewness value and the kurtosis value of the plurality of values of the same feature parameter and to train the third model M3, so that the accuracy of the third model M3 can be enhanced.

The data preprocessing step S15 includes assessing whether a number of the plurality of feature information of each of the plurality of medical datasets is equal to a present number or not. When the number of the plurality of feature information of each of the plurality of medical datasets is smaller than the present number, an average value can be filled corresponding to one of the plurality of feature information being missing based on an imputation procedure. When the number of the plurality of feature information of each of the plurality of medical datasets is larger than the present number, and one of the plurality of feature information includes at least two values, the at least two values can be replaced with another average value of the at least two values.

In detail, each the plurality of medical datasets can include the clinical data of the plurality of patients (that is, the plurality of feature information) collected from the medical institutions, and the plurality of feature information can include the lung infiltration probability, the blood inspection data D2, the vital signs data D3 and the respiratory data D4. When the number of the plurality of feature information and the types of parameters of the plurality of patients are not completely the same, that are, the types or the values of the plurality of feature information of parts of the plurality of patients are missing, or one of the types of the plurality of feature information of the plurality of patients includes more than one value, the plurality of feature information can be preprocessed by the data preprocessing step S15, and thus all of the number and the types of the plurality feature information are completely corresponded so as to process the probability generating step S16.

For example, when the at least one feature information of one of the plurality of medical datasets of one patient is missing (for example, the oxygenation ratio of the blood inspection data D2), the medical datasets of the missing feature information can be filled in based on an average value obtained from the same feature information (that is, the oxygenation ratio of the blood inspection data D2) of the medical datasets of other patients in the data preprocessing step S15 by the imputation procedure.

When one of the plurality of feature information (for example, the oxygenation ratio of the blood inspection data D2) of the medical datasets of one patient has two values, an average value of the aforementioned two values can be calculated in the data preprocessing step S15, and the aforementioned two values can be replaced with the average value.

In the third example, the imputation procedure can be a K-Nearest Neighbor (KNN) algorithm. The data preprocessing step S15 is performed after the lung infiltration determining step S14 and before the probability generating step S16, but the present disclosure is not limited thereto. Hence, the ARDS suffering probability can be assessed based on the X-ray image and the real-time clinical data in the acute respiratory distress syndrome evaluating method S10$a$ of the present disclosure, so that the survival rate of the patient can be enhanced by the interventional treatment in early disease course.

In the third example, the X-ray image data D1, the blood inspection data D2, the vital signs data D3 and the respiratory data D4 are obtained from 366 medical records of patients diagnosed with the acute respiratory distress syndrome within 24 hours before being diagnosed and 1567 medical records of patients who did not suffer the acute respiratory distress syndrome in the 24 hours before and after admission to an intensive care unit in China Medical University Hospital. The verification results of the ARDS suffering probability can be generated by training the aforementioned medical records through the acute respiratory distress syndrome evaluating method S10$a$, and the aforementioned results are shown in Table 1. In the third example, the statistical features include the average value, the standard deviation, the skewness value and the kurtosis value, but the present disclosure is not limited thereto.

TABLE 1

|  | Verification group | Test group |
|---|---|---|
| K-fold cross-validation analysis | 5 folds | Test |
| Feature number | 19 | 19 |
| Accuracy (ACC) | 0.911~0.935 | 0.903 |
| AUC | 0.901~0.923 | 0.878 |
| Specificity | 0.917~0.943 | 0.918 |
| Recall ratio | 0.88~0.906 | 0.837 |
| f1 score | 0.791~0.841 | 0.766 |

As shown in Table 1, the aforementioned medical records can be divided into five-folds so as to serve as the verification group and the test group according to the K-fold cross-validation analysis. The feature number is 19, wherein the accuracy, the Area Under the receiver operating characteristic Curve (AUC), the specificity, the recall ratio and f1 score of the ARDS suffering probability are all reached to 0.9. Given above, the acute respiratory distress syndrome evaluating method S10$a$ of the present disclosure can be accurately evaluated whether the patient suffers the acute respiratory distress syndrome or not according to the medical records thereof, and has excellent potential of clinical application.

From the above examples, the acute respiratory distress syndrome evaluating method and the system of the present disclosure have following advantages. First, the ARDS suffering probability can be immediately diagnosed according to the dynamical disease course so as to provide the corresponding treatment. Second, the ARDS suffering probability can be assessed according to the X-ray image and the real-time clinical data so that the survival rate of the patient can be enhanced by interventional treatment in early disease course.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An acute respiratory distress syndrome (ARDS) evaluating method, comprising:
an image preprocessing step comprising driving a processor to input an X-ray image data to a first model so as to generate an X-ray partial image;
a lung infiltration determining step comprising driving the processor to input the X-ray partial image to a second model so as to generate a lung infiltration probability and a lung infiltration region image;
a probability generating step comprising driving the processor to input the lung infiltration probability, a blood inspection data, a vital signs data and a respiratory data to a third model so as to generate an ARDS suffering probability; and
an evaluating step comprising driving the processor to calculate the lung infiltration region image and the ARDS suffering probability so as to obtain an evaluating result;
wherein the first model is an Efficient-UNet model, the second model is an Efficient-Net model and comprises a Convolutional Block Attention Module (CBAM), and the third model is an extreme Gradient Boosting model.

2. The acute respiratory distress syndrome evaluating method of claim 1, wherein the X-ray image data is cut by the first model so as to obtain the X-ray partial image, and the X-ray partial image consists of a lung region image.

3. The acute respiratory distress syndrome evaluating method of claim 1, further comprising:
a model training step, comprising:
a first training step comprising driving the processor to train the first model based on an X-ray image training set and a lung X-ray image training set;
a second training step comprising driving the processor to train the second model based on a lung infiltration X-ray image training set and the lung X-ray image training set; and
a third training step comprising driving the processor to train the third model based on a plurality of medical datasets, wherein each of the plurality of medical datasets comprises the lung infiltration probability, the blood inspection data, the vital signs data and the respiratory data.

4. The acute respiratory distress syndrome evaluating method of claim 3, wherein the lung X-ray image training set comprises
a plurality of labelled chest X-ray images.

5. The acute respiratory distress syndrome evaluating method of claim 3, wherein the third training step further comprises:
driving the processor to calculate the plurality of medical datasets so as to obtain an average value, a standard deviation, a skewness value and a kurtosis value of at least one of the blood inspection data, the vital signs data and the respiratory data of each of the plurality of medical datasets, and then to train the plurality of medical datasets and the average value, the standard deviation, the skewness value and the kurtosis value of the at least one of the blood inspection data, the vital signs data and the respiratory data of each of the plurality of medical datasets so as to establish the third model.

6. The acute respiratory distress syndrome evaluating method of claim 3, wherein each of the plurality of medical datasets comprises a plurality of feature information, and the acute respiratory distress syndrome evaluating method further comprises:
a data preprocessing step comprising driving the processor to assess whether a number of the plurality of feature information of each of the plurality of medical datasets is equal to a present number or not;
when the number of the plurality of feature information of each of the plurality of medical datasets is smaller than the present number, the processor is driven to fill in an average value corresponding to one of the plurality of feature information being missing based on an imputation procedure; and
when the number of the plurality of feature information of each of the plurality of medical datasets is larger than the present number, and one of the plurality of feature information comprises at least two values, the processor is driven to replace the at least two values with another average value of the at least two values.

7. The acute respiratory distress syndrome evaluating method of claim 6, wherein the imputation procedure is a K-Nearest Neighbor (KNN) algorithm.

8. An acute respiratory distress syndrome evaluating system, comprising:
a database for accessing a first model, a second model, a third model, an X-ray image data, a blood inspection data, a vital signs data and a respiratory data; and
a processor signally connected to the database and configured to perform an acute respiratory distress syndrome evaluating method, wherein the acute respiratory distress syndrome evaluating method comprises:
an image preprocessing step comprising inputting the X-ray image data to the first model so as to generate an X-ray partial image;
a lung infiltration determining step comprising inputting the X-ray partial image to the second model so as to generate a lung infiltration probability and a lung infiltration region image;
a probability generating step comprising inputting the lung infiltration probability, the blood inspection data, the vital signs data and the respiratory data to the third model so as to generate an ARDS suffering probability; and an evaluating step comprising calculating the lung infiltration region image and the ARDS suffering probability so as to obtain an evaluating result;

wherein the first model is an Efficient-UNet model, the second model is an Efficient-Net model and comprises a Convolutional Block Attention Module (CBAM), and the third model is an extreme Gradient Boosting model.

9. The acute respiratory distress syndrome evaluating system of claim 8, wherein the X-ray image data is cut by the first model so as to obtain the X-ray partial image, and the X-ray partial image consists of a lung region image.

10. The acute respiratory distress syndrome evaluating system of claim 8, wherein the acute respiratory distress syndrome evaluating method further comprises:

a model training step, comprising:

a first training step comprising training the first model based on an X-ray image training set and a lung X-ray image training set;

a second training step comprising training the second model based on a lung infiltration X-ray image training set and the lung X-ray image training set; and a third training step comprising training the third model based on a plurality of medical datasets, wherein each of the plurality of medical datasets comprises the lung infiltration probability, the blood inspection data, the vital signs data and the respiratory data.

11. The acute respiratory distress syndrome evaluating system of claim 10, wherein the lung X-ray image training set comprises a plurality of labelled chest X-ray images.

12. The acute respiratory distress syndrome evaluating system of claim 10, wherein the third training step further comprises:

calculating the plurality of medical datasets so as to obtain an average value, a standard deviation, a skewness value and a kurtosis value of at least one of the blood inspection data, the vital signs data and the respiratory data of each of the plurality of medical datasets, and then training the plurality of medical datasets and the average value, the standard deviation, the skewness value and the kurtosis value of the at least one of the blood inspection data, the vital signs data and the respiratory data of each of the plurality of medical datasets so as to establish the third model.

13. The acute respiratory distress syndrome evaluating system of claim 10, wherein each of the medical datasets comprises a plurality of feature information and the acute respiratory distress syndrome evaluating method further comprises:

a data preprocessing step comprising assessing whether a number of the plurality of feature information of each of the plurality of medical datasets is equal to a present number or not;

when the number of the plurality of feature information of each of the plurality of medical datasets is smaller than the present number, an average value corresponding to one of the plurality of feature information being missing is filled therein based on an imputation procedure; and when the number of the plurality of feature information of each of the plurality of medical datasets is larger than the present number, and one of the plurality of feature information comprises at least two values, the at least two values are replaced with another average value of the at least two values.

14. The acute respiratory distress syndrome evaluating system of claim 13, wherein the imputation procedure is a K-Nearest Neighbor (KNN) algorithm.

* * * * *